United States Patent [19]
Victor

[11] Patent Number: 5,204,093
[45] Date of Patent: Apr. 20, 1993

[54] SHAVING CREAM COMPOSITION FOR THE TREATMENT OF ACNE VULGARIS AND PSEUDOFOLLICULITIS BARBAE AND METHOD OF PRODUCING AND USING SAME

[76] Inventor: Steven A. Victor, 301 E. 79th St., New York, N.Y. 10021

[21] Appl. No.: 728,031

[22] Filed: Jul. 2, 1991

Related U.S. Application Data

[63] Continuation of Ser. No. 334,700, Apr. 6, 1989, abandoned.

[51] Int. Cl.$^5$ .................. A61K 7/15; A61K 31/19
[52] U.S. Cl. .................................... 424/73; 424/405; 514/714; 514/859
[58] Field of Search ............... 424/73, 405; 514/714, 514/859

[56] References Cited

U.S. PATENT DOCUMENTS

| | | | |
|---|---|---|---|
| 3,535,422 | 10/1970 | Cox et al. | 514/714 |
| 4,056,611 | 11/1977 | Young | 514/714 |
| 4,189,501 | 2/1980 | Fulton, Jr. | 514/714 |
| 4,228,163 | 10/1980 | Bliss | 514/171 |
| 4,609,674 | 9/1986 | Gupte | 514/714 X |
| 4,640,932 | 2/1987 | Fong et al. | 514/714 |
| 4,733,466 | 3/1988 | Fletcher, Jr. | 30/34.2 |
| 4,778,674 | 10/1988 | Gupte et al. | 424/45 |
| 4,803,228 | 2/1989 | Jacquet et al. | 514/714 |
| 4,857,302 | 8/1989 | Decker, Jr. et al. | 514/714 |
| 5,019,567 | 5/1991 | Philippe et al. | 514/164 |

FOREIGN PATENT DOCUMENTS

| | | | |
|---|---|---|---|
| 1165244 | 4/1984 | Canada . | |
| 13459 | 7/1980 | European Pat. Off. | 514/714 |
| 8300628 | 3/1983 | United Kingdom | 514/356 |

OTHER PUBLICATIONS

Journal of Pharmaceutical Science article by Bollinger et al. entitled, "Benzoyl Peroxide Stability in Pharmaceutical Gel Preparations."

*Primary Examiner*—Thurman K. Page
*Assistant Examiner*—Neil Levy
*Attorney, Agent, or Firm*—Morgan & Finnegan

[57] ABSTRACT

A non-gritty brushless, or gel-foam shaving cream composition is provided containing a therapeutically effective amount of benzoyl peroxide. The shaving cream composition can be used in the topical treatment of acne vulgaris, pseudofolliculitis barbae and other skin conditions.

31 Claims, No Drawings

SHAVING CREAM COMPOSITION FOR THE TREATMENT OF ACNE VULGARIS AND PSEUDOFOLLICULITIS BARBAE AND METHOD OF PRODUCING AND USING SAME

This is a continuation of co-pending application Ser. No. 07/334,700, filed on Apr. 6, 1989, and now abandoned.

FIELD OF INVENTION

This invention relates to brushless or gel-foam shaving cream compositions and methods of producing and using the same. More particularly, this invention relates to shaving cream compositions used in the treatment of acne vulgaris and pseudofolliculitis barbae.

BACKGROUND OF INVENTION

There are generally three types of shaving creams each having their own distinct properties: lathering; brushless or non-lathering; and post-foaming gel, or gel foam.

Lathering shaving creams are generally concentrated dispersions of alkali metal soaps in glycerol and water. The lathering effect exhibited by these shaving creams results from mixing stearic acid with a coconut oil fatty acid in a ratio of approximately 1 part to 3 parts. These shaving creams normally contain between about 30 and 50% soap and either potassium hydroxide, sodium hydroxide, or a combination of the two to saponify the fatty acids. As with other types of shaving creams, the formulation of a lathering shaving cream may include lubricants, fragrances, preservatives, foam stabilizers, humectants and the like.

Brushless, or non-lathering shaving creams are basically oil-water emulsions. These shaving creams have a lower pH than conventional lathering shaving creams and therefore, typically cause less irritation during and after shaving. Lower pH results from the absence of potassium hydroxide or sodium hydroxide. Lubricants, fragrances preservatives, humectants and other materials commonly used in a shaving cream mixture can also be present in this type of shaving cream.

The third type of shaving cream is the post-foaming gel, or gel-foam shaving cream. This is basically an aqueous dispersion. With this type of shaving cream, lather is typically formed in situ on the surface of the skin. The lathering effect is believed to result from the vaporization of low-boiling point aliphatic hydrocarbons.

Acne vulgaris is a common dermatological condition which affects a large portion of the population. The specific cause of this condition is still unknown. However, there is general agreement that the following can contribute to acne vulgaris: 1) an individual's genetic predisposition to acne; 2) the size of an individual's sebaceous gland, (see Cunliffe et al., The Acne: Clinical Features, Pathogensis and Treatment, 62, 66–67 (1975)); 3) the type and quantity of bacteria within the hair follicle, (see Marples et al., "Control of Free Fatty Acid in Human Surface Lipids..." 56 J. Investigative Dermatology 127–31 (1971)); 4) the androgenic stimulation of sebum, (see Shalita, "Acne Vulgaris Current Concepts in Pathogenesis Treatment International", 15 J. of Dermatology 182–87 (1976)); and 5) alterations to the keratinization process, (see Holms et al., "Philosebaceous Duct Obstruction in Acne", 37 British J. of Dermatology 327–33)).

Acne typically results in the formation of papules, pustules, or cysts which are often contaminated with bacteria. Such a condition is at best unsightly and at worst unhealthy, and as such, an effective treatment has been sought for many years.

Benzoyl peroxide, $(C_6H_5CO)_2O_2$, is a colorless, odorless, tasteless, crystalline solid which is generally stable at room temperature. Benzoyl peroxide has been first considered for the treatment of acne vulgaris since at least 1934. Vehicles used in the topical application of benzoyl peroxide include creams, lotions and gels. For example, U.S. Pat. No. 4,778,674 discloses a dry aerosol foam containing benzoyl peroxide for use in the treatment of acne vulgaris. However, the prior art methods and compositions have not been very successful in treating acne, either because of the compositions employed, the various methods of application, both, or for some other reasons.

In addition to acne, other serious skin conditions are pseudofolliculitis barbae, pseudofolliculitis of the beard, or pseudofolliculitis capitae, all more commonly known as "razor bumps." These conditions generally result from ingrown hairs. They typically occur on the human neck, jowl and chin, and are characterized by erythematous lesions, firm papules, pustules, or cysts which contain buried hairs. While these condition afflict many, it is particularly troublesome for those with curvy or curly hair. Curvy or curly hair, upon growing out of the hair follicle curves back in an arch, and penetrates the skin. This results in an inflammatory reaction which ultimately leads to the development of "razor bumps."

Past remedies for treating "razor bumps" included the use of depilatories, such as barium sulfide powder or calcium thioglycollate. However, it has been suggested that topical application of antibacterial agents such as tetracycline or petrolatum resulted in insignificant long-term effects, and therefore would be ineffective if used as a depilatory.

Though a depilatory has been used with some success in treating "razor bumps," such treatment can only be used on an infrequent basis by most people. Depilatories can result in skin irritation and generally should only be administered no sooner than every three days. This application schedule, however, will not alleviate the irritation in most people. Furthermore, even if such a schedule could be tolerated, it could not be used to treat pseudofolliculitis barbae. The growth of the beard during the period of time between depilatories would result in the person having a very unkempt appearance.

Other methods of treating pseudofolliculitis barbae have been attempted. For example, U.S. Pat. No. 4,228,163 discloses use of a synergistic combination of benzoyl peroxide and chlorohydroxyquinoline.

As a result of these unsightly and unhealthy conditions which afflict a large portion of today's society, it would be highly desirable to develop a composition which would effectively treat and control both acne vulgaris and pseudofolliculitis barbae. It would also be highly desirable that such composition be cosmetically pleasant, commercially acceptable, easy to use, easy to apply and have the ability to be used on a daily basis.

Accordingly, it is an object of this present invention to provide a novel and unique brushless or gel-foam shaving cream composition which is both physically and chemically stable when admixed with benzoyl peroxide in quantities which are therapeutically effective for the treatment of acne vulgaris or pseudofolliculitis barbae.

It would also be highly desirable to produce such a composition in a manner which would not degrade due to the presence of benzoyl peroxide, and further would not result in deterioration of the shaving cream system.

It would also be highly desirable to produce such a composition that would be easy to apply and non-gritty.

A further object of the present invention is to provide a new and improved method of preparing brushless or gel-foam shaving cream compositions which can be used for the treatment of acne vulgaris and pseudofolliculitis barbae.

A still further object of this invention is to provide an improved method for applying compositions which would be effective in the treatment of acne vulgaris and pseudofolliculitis.

These and still further objects shall become readily apparent following the detailed description of the present invention.

SUMMARY OF INVENTION

The present invention relates to a brushless or gel-foam shaving cream composition and method of producing and using said shaving cream compositions containing benzoyl peroxide which can be used in the treatment of acne vulgaris and pseudofolliculitis barbae.

According to the present invention it has been unexpectedly discovered that using benzoyl peroxide in shaving cream provides advantageous results not heretofore obtained.

Without wishing to be limited by theory, it is believed that the greatly improved results are obtained because shaving cream, used in conjunction with the shaving process, i.e. with a typical razor blade, permits the active ingredient, benzoyl peroxide, to penetrate the sebaceous duct through the follicular opening in the skin. Furthermore, the effectiveness of benzoyl perioxide is increased when it penetrates the stratum corneum, or top layer of the epidermis. The action of a razor on the human skin removes the top layer of the epidermis thereby allowing the benzoyl peroxide to penetrate the hair follicle. This penetration allows the benzoyl peroxide to be a much more effective antibiotic and keratolyic agent. This increased effectiveness has been found to achieve superior results, heretofore unknown, in the treatment of acne vulgaris and pseudofolliculitis barbae.

The shaving cream composition of the invention can contain one or more carrier vehicles, a therapeutically effective amount of benzoyl peroxide and additional ingredients commonly employed in the manufacture of shaving cream.

DETAILED DESCRIPTION

The present invention provides a unique and highly stable mixture in which a therapeutically effective amount of benzoyl peroxide is dispersed in a specially formulated brushless or gel-foam shaving cream. The resulting product is a non-gritty, easy to apply, easy to use and cosmetically pleasing shaving cream which can be effectively used in the treatment of acne vulgaris and pseudofolliculitis barbae on a daily basis. The shaving cream as disclosed by this invention can be comprised of approximately 0.25 to approximately 50 weight percent benzoyl peroxide.

The shaving cream composition of this invention may also be composed of numerous other ingredients which are commonly employed in the manufacture of shaving cream. The only limitation on these additional components is that their presence should not adversely affect the unique properties, qualities and stability of the present invention. Therefore, the presence of substantial quantities of potassuim hydroxide or sodium hydroxide, which might adversely affect the benzoyl peroxide, should not be present.

The brushless or non-lathering shaving cream composition of this invention can contain the following; approximately 0.25 to about 50%, preferably 2.5 to 20%, and more preferably 5 to 10% by weight benzoyl peroxide; typically 4 to 10% by weight of a lubricant; typically 10 to 25%, by weight of a binder; typically 2 to 10% by weight of a humectant; typically 0 to 5% by weight of an emollient; typically 0–5% by weight of a soap; typically 0 to 5% of a surfactant; typically 1 to 5% by weight of a neutralizer; and typically 60 to 70% by weight of deionized water. Fragrances, preservatives, hydrolized animal proteins and cooling agents can also be added.

The gel-foam, or post foaming gel shaving cream composition of this invention can contain the following; approximately 0.25 to 50%, preferably 2.5 to 20% and more preferably 5 to 10% by weight of benzoyl perioxide; typically 7.8 to 9% by weight of a binder; typically 1% by weight of a stablizer; typically 0.25 to 0.3% by weight of a gelling or thickening agent; typically 2.75% by weight of a preservative; typically 13.3% by weight of a humectant; typically 4.2 to 4.75% by weight of a neutralizer; 61.4 to 62.95% by weight of deionized water; and typically 2.75% by weight a low boiling point aliphatic hydrocarbon. Additionally, fragrances, soaps, hydrolized animal proteins and cooling agents can also be added.

Lubricants are typically used in the above formulation to lubricate the area to be shaved so that the razor will travel with as little resistance as possible. Typical lubricants which can be used in the shaving cream compositions of this invention include mineral oil, and long chain fatty acid esters.

Binders are typically used to provide superfatting action and assist the characteristic pearlescent appearance of the shaving cream. Stearic acid and palmetic acid are commonly used as binder, although other suitable binders may be used.

Gelling or thickening agents are typically used to improve the stability of the shaving cream. Typical of such agents included fused silica (Carbopol 934), anhydrous silica and hydroxyalkyl cellulose.

Humectants generally promote the retention of water and are particularly desirable in a shaving cream. Common humectants include proplyene glycol, sorbitol, glycerol and glycerine.

Emollients are typically used to soften and protect the skin. Common emollients applicable to the present invention include lanolin, cetyl alcohol and stearyl alcohol.

To improve the stability of the emulsion and increase a beard wetting and rinsibility, surfactants can be added to the shaving cream mixture. Examples of such components include diisopropyl dimerate, glycerol monostearate, polyoxyethylene (2) cetyl ether and fatty acid amides.

Hydrolyzed animal proteins can also be added to the shaving creams of this invention. Such an ingredient aids in the coating and softening of the hair to be shaved.

Preservatives which can be used in the shaving cream compositions of this invention include methyl paraben, diazolidinyl urea and propyl paraben. Neutralizers can include triethanolamine, propylene glycol dipelargonate and polyethylene glycol 15 cocamine.

Examples of low boiling point aliphatic hydrocarbons include, but are not limited to, n-butane and n-pentane.

Not all of these ingredients need to be present to produce the unique properties and applications of the present invention. In most formulations, one or more of the above mentioned ingredients will be absent in order to produce a shaving cream composition with a particular feel or desired texture Furthermore, some of the ingredients may serve a dual purpose For example, an ingredient used as a lubricant in one formulation may be used as a beard softener in another. Likewise, a gelling agent in one shaving cream may be used as a stabilizer in another. The applicant's present invention contemplates and anticipates such variations.

Generally, post-foaming gel, or gel-foam shaving creams will have components in proportions similar to those present in a brushless, or nonfoaming shaving cream. A difference is the presence of a saturated low boiling point aliphatic hydrocarbon in the gel-foam composition. The saturated alphatic hydrocarbon can be present in amount of approximately 2 to 4% by weight. Examples of saturated aliphatic hydrocarbons which can be used in the present invention include n-butane and n-pentane.

The present brushless shaving cream composition can also be used with a typical aerosol delivery system to produce a pressurized foamable shaving cream which when discharged through an aerosol container will provide a cosmetically pleasant foam. As such, any propellant which is typically used in an aerosol delivery system may be used with the invention. Among the propellants which can be used are halogenated hydrocarbons, such as chlorinated and fluorinated methanes, ethanes and butanes. Similiarly unhalogenated hydrocarbons, such as propane or isobutane can also be employed. In certain cases it may be desirable to use two or more propellants so that there will be sufficient pressure to aid in the delivery of certain shaving cream compositions. The quantity of propellant can vary depending on the properties and consistency required of the shaving cream composition. Therefore, the quantity of propellent can vary from at least about 1% up to approximately 10%.

The following is an example of the brushless shaving cream. In the example, the percentage is expressed as percentage by weight.

EXAMPLE I

| Ingredient | Percentage |
| --- | --- |
| Mineral oil | 9.50 |
| Diisopropyl dimerate | 1.00 |
| Stearic acid | 14.50 |
| Deionized water | 64.35 |
| Carbopol 934 | 0.50 |
| Triethanolamine | 2.90 |
| Polyethylene glycol 15 cocamine | 0.50 |
| Fragrance | 0.25 |
| Methyl paraben | 0.30 |
| Propyl paraben | 0.20 |
| Diazolidinyl urea | 0.50 |
| Benzoyl peroxide | 5.50 |

An example of a shaving cream consistent with the scope of the invention can be produced as follows:

EXAMPLE 2

20 grams of Carbopol 934 is thoroughly mixed with 1,600 grams of purified water. To this resulting mixture, 120 grams of triethanolamine, 20 grams of polyethylene glycol 15 cocamine, 12 grams of methyl paraben, 8 grams of propyl paraben and 20 grams of diazolidinyl urea are added. The resulting mixture shall be referred to as Mixture A.

380 grams of mineral oil, 580 grams of stearic acid and 40 grams of diisopropyl dimerate are mixed together to form what will be referred to as Mixture B.

Mixtures A and B are heated to a temperature of 75° C. Mixture A is then added to Mixture B to form Mixture C. Mixture C is vigorously agitated and allowed to cool to a temperature of 50° C. At 50° C., 10 grams of a fragrance is added to Mixture C.

A mixture of 973 grams of benzoyl peroxide and 280 grams of water is milled until smooth and then subsequently added to Mixture C. The resulting mixture is then milled to produce a shaving cream composition which is non-gritty, cosmetically pleasing and easy to apply.

The brushless shaving cream composition of this invention can also be put into a typical aerosol delivery system to produce a pressurized foamable shaving cream which when discharged through an aerosol container will provide a foam. The following example relates to a unique aerosol shaving cream which will be effective in the treatment of acne vulgaris and pseudofolliculitis barbae. In the example, the percentage is expressed as percentage by weight.

EXAMPLE 3

| Ingredient | Percentage |
| --- | --- |
| Mineral oil | 9.03 |
| Diisopropyl dimerate | .95 |
| Stearic acid | 13.78 |
| Deionized water | 61.09 |
| Carbopol 934 | .48 |
| Triethanolamine | 2.76 |
| Polyethylene glycol 15 cocamine | .48 |
| Fragrance | .24 |
| Methyl paraben | .29 |
| Propyl paraben | .19 |
| Diozolidinyl urea | .48 |
| Benzoyl peroxide | 5.23 |
| Isobutane | 5.00 |

The following is an example of a gel-foam, or post foaming gel shaving cream. In the example, the percentage is expressed as percentage by weight.

EXAMPLE 4

| Ingredient | Percentage |
| --- | --- |
| Stearic Acid | 2.000 |
| Palmitic Acid | 5.800 |
| Polyoxyethylene (2) cetyl ether | 1.000 |
| Hydroxyalkyl cellulose | .067 |
| Carbopol 934 | .180 |
| Propylene glycol dipelargonate | 2.750 |
| Sorbital | 10.000 |
| Propylene glycol | 3.300 |
| Triethanolamine | 4.200 |
| Deionized Water | 62.953 |
| n-butane | .550 |
| n-pentane | 2.200 |
| Benzoyl peroxide | 5.000 |

An example of gel-foam shaving cream consistent with the scope of the invention can be produced as follows:

EXAMPLE 5

Stearic acid, palmitic acid and polyoxyethylene (2) cetyl ether are heated to approximately 80° C. at which point sorbitol and triethanolamine are added to form Solution A. A solution containing hydroxyalkyl cellulose, benzoyl peroxide and propylene glycol and a solution of carbopol 934 and water are added to Solution A at a temperature of 27° C. to form Mixture B.

The low boiling point aliphatic hydrocarbons, n-butane and n-pentane are dispersed in an equal volume of propylene glycol at a temperature of 4° C. The resulting hydrocarbon mixture then is added to Mixture B in such a way as to avoid trapping air within the resulting gel. This gel is then transfered to the inner compartment of a barrier aerosol dispenser and the valve is crimped in place. The outer compartment is the pressurized with sufficient propellant to have a pressure of approximately 46 psi at 25° C.

One preferred use of the products of the invention is accomplished through the application of the novel shaving cream composition to the area affected by acne vulgaris and/or pseudofolliculitis barbae once daily. The area to which the product of the invention is to be applied is first washed thoroughly with a mild non-medicated cleanser or soap. The shaving cream composition is then applied evenly in a thin layer using a circular motion and lathered up by the fingertips. The affected area is then shaved with a razor in a normal manner.

The shaving cream compositions of this invention provide a more effective method of treating acne vulgaris and pseudofolliculitis barbae compared to other topical applications of benzoyl peroxide. The benzoyl peroxide is most effective in the treatment of acne vulgaris and pseudofolliculitis barbae when it penetrates the stratum corneum, or top layer of the epidermis. The top layer of the epidermis normally acts as a barrier against the penetration of benzoyl peroxide. However, during the act of shaving, the top later of the epidermis is removed, allowing the benzoyl peroxide to penetrate into the hair follicle. This penetration allows the benzoyl peroxide to act as a more effective antibiotic and keratolytic agent in the treatment of acne vulgaris and pseudofolliculitis barbae.

The following examples are illustrative of the invention.

EXAMPLE 6

Twenty male caucasians aged 16 to 35 with acne vulgaris and twenty males of the black race with pseudofolliculitis barbae comprised the test group. Each was shaved daily with the benzoyl peroxide brushless shaving cream composition described in Example 1. The patient's face was first washed with warm water and a non-medicated mild soap. The face was then rinsed. A thin layer of the shaving cream was evenly applied to the face and lathered up using a circular motion of the fingertips. The face was then shaved using a straight edge razor in a normal manner. Upon completion of the shaving, the face was rinsed with cool water.

All of the patients noted a clinical improvement in their condition, either acne vulgaris or pseudofolliculitis barbae, within 2-3 days. A clinical evaluation by a dermatologist, after one week of treatment using the shaving cream composition of this invention revealed an improvement of 80-90% in the initial condition of the patients skin.

EXAMPLE 7

The patient's face is first washed with warm water and a non-medicated soap. The face is then rinsed. A thin layer of the gel foam shaving cream composition described in Example 4 is applied evenly to the face and lathered up using a circular motion of the fingertips. The face is then shaved using a straight edge razor in a normal manner. Upon completion of the shaving, the face is rinsed with cool water.

Although the present invention has been described with reference to particular embodiments and examples, it will be apparent to those skilled in the art that variation and modifications of this invention can be substituted without departing from the principles and true spirit of the invention as defined in the appended claims.

I claim:

1. A method of treating acne vulgaris or pseudofolliculitis barbae in humans, comprising the steps of:
    applying to the skin a brushless, or non-lathering shaving cream containing in stable admixture therewith a therapeutically effective amount of benzoyl peroxide; and
    removing the brushless, or non-lathering shaving cream by shaving with a straight-edge razor.

2. A method of treating acne vulgaris or pseudofolliculitis barbae in humans, comprising the steps of:
    applying to the skin a brushless, or non-lathering shaving cream composition consisting essentially of in percent by weight:
    about 4 to 10% of a lubricant;
    about 10 to 25% of a binder;
    about 0 to 1% of a gelling or thickening agent;
    about 50 to 65% of deionized water;
    about 2 to about 10% of a humectant;
    about 0 to about 0.5% of a preservative;
    about 0 to about 5% of a emollient;
    about 1 to about 5% of a neutralizer;
    about 0 to about 5% of a surfactant; and
    about 0.25 to about 50% of benzoyl peroxide; and
    removing the brushless, or non-lathering shaving cream by shaving with a straight-edge razor.

3. A method of treating acne vulgaris or pseudofolliculitis barbae in humans, comprising the steps of:
    applying to the skin a foamable aerosol brushless shaving cream containing in stable admixture therewith a therapeutically effective amount of benzoyl peroxide; and
    removing the foamable aerosol brushless shaving cream by shaving with a straight-edge razor.

4. A composition for the treatment of acne vulgaris or pseudofolliculitis barbae in humans, comprising a brushless, or non-lathering shaving cream composition, consisting essentially of in percent by weight:
    about 4 to 10% of a lubricant;
    about 10 to 25% of a binder;
    about 0 to 1% of a gelling or thickening agent;
    about 50 to 65% of deionized water;
    about 2 to about 10% of a humectant;
    about 0 to about 0.5% of a preservative;
    about 0 to about 5% of a emollient;
    about 1 to about 5% of a neutralizer;
    about 0 to about 5% of a surfactant; and
    about 0.25 to about 50% of benzoyl peroxide.

5. A shaving cream composition according to claim 4 wherein the lubricant is selected from the group consisting of mineral oil and a long chain fatty acid ester.

6. A shaving cream composition according to claim 4 wherein the preservative is selected from the group consisting of methyl paraben, propyl paraben and diazolidinyl urea and combinations thereof.

7. A shaving cream composition according to claim 4 wherein the binder is selected from the group consisting of stearic acid and a palmitic acid and combinations thereof.

8. A shaving cream composition according to claim 4 wherein the gelling or thickening agent is selected from the group consisting of fused silican, anhydrous silica and hydroxyalkyl celluslose.

9. A shaving cream composition according to claim 4 wherein the humectants are selected from the group consisting of propylene glycol, sorbitol and glycerol and combinations thereof.

10. A shaving cream composition according to claim 4 wherein the emollients are selected from the group consisting of lanolin, cetyl alcohol and stearyl alcohol and combinations thereof.

11. A shaving cream composition according to claim 4 wherein the neutralizers are selected from the group consisting of triethanolamine, propylene glycol dipelargonate and polyethylene glycol 15 cocamine and combinations thereof.

12. A shaving cream composition according to claim 4 wherein the surfactant is selected from the group consisting of diisopropyl dimerate, glycerol monostearate, polyoxyethylene (2) cetyl ether and fatty acid amides and combinations thereof.

13. A brushless composition for the treatment of acne vulgaris or pseudofolliculitis barbae in humans, comprising a foamable aerosol brushless shaving cream composition, consisting essentially of in percent by weight:
about 4 to about 10% of a lubricant;
about 10 to about 25% of a binder;
about 0 to about 1% of a gelling or thickening agent;
about 50 to about 60% of deionized water;
about 0 to about 5% of a emollient;
about 0 to about 0.5% of a preservative;
about 0 to about 5% of a soap;
about 0 to about 5% of a surfactant;
about 2 to about 10% of a humectant;
about 0.25% to about 50% of benzoyl peroxide; and
about 2 to about 4% of a propellant.

14. A shaving cream composition according to claim 13 wherein the lubricant is selected from the group consisting of mineral oil and a long chain fatty acid ester and combinations thereof.

15. A shaving cream composition according to claim 13 wherein the binder is selected from the group consisting of stearic acid and palmitic acid and combinations thereof.

16. A shaving cream composition according to claim 13 wherein the gelling or thickening agent is selected from the group consisting of fused silica anhydrous silica and hydroxyalkyl cellulose and combinations thereof.

17. A shaving cream composition according to claim 13 wherein the emollients are selected from the group consisting of lanolin, cetyl alcohol and stearyl alcohol and combinations thereof.

18. A shaving cream composition according to claim 13 wherein the preservative is selected from the group consisting of methyl paraben, propyl paraben and diazolidinyl urea and combinations thereof.

19. A shaving cream composition according to claim 13 wherein the surfacant is selected from the group consisting of diisopropyl dimerate, glycerol monostearate, polyoxyethylene (2) cetyl ether and fatty acid amides and combinations thereof.

20. A shaving cream composition according to claim 13 wherein the humectants are selected from the group consisting of propylene glycol, sorbitol and glycerol and combinations thereof.

21. A method of treating acne vulgaris or pseudofolliculitis barbae in humans, comprising the steps of:
applying to the skin a foamable aerosol brushless shaving cream composition consisting essentially of in percent by weight:
about 4 to about 10% of a lubricant;
about 10 to about 25% of a binder;
about 0 to about 1% of a gelling or thickening agent;
about 50 to about 60% of deionized water;
about 0 to about 5% of a emollient;
about 0 to about 0.5% of a preservative;
about 0 to about 5% of a soap;
about 0 to about 5% of a surfactant;
about 2 to about 10% of a humectant;
about 0.25% to about 50% of benzoyl peroxide; and
about 2 to about 4% of a propellant; and
removing the foamable aerosol brushless shaving cream by shaving with a straight-edge razor.

22. A method of treating acne vulgaris or pseudofolliculitis barbae in humans, comprising the steps of:
applying to the skin a gel-foam shaving cream containing in stable admixture therewith a therapeutically effective amount of benzoyl peroxide; and
removing the gel-foam shaving cream by shaving with a straight-edge razor.

23. A composition for the treatment of acne vulgaris or pseudofolliculitis barbae in humans, comprising a gel-foam shaving cream composition, consisting essentially of in percent by weight:
about 0.25 to about 3% of a gelling or thickening agent;
about 7.8 to about 9.0% of a binder;
about 1% of a stabilizer;
about 2.75% of a preservative;
about 0.25% to about 50% of benzoyl peroxide;
about 13.3% of a humectant;
about 4.2 to about 4.75% of a neutralizer;
about 61.4 to 62.95% of deionized water; and
about 2.75% of a low boiling point aliphatic hydrocarbon.

24. A shaving cream composition according to claim 23 wherein the gelling or thickening agent is selected from the group consisting of fused silica, anhydrous silica and hydroxyalkyl cellulose and combinations thereof.

25. A shaving cream composition according to claim 23 wherein the binder is selected from the group consisting of stearic acid and palmitic acid and combinations thereof.

26. A shaving cream composition according to claim 23 wherein the stabilizer is selected from the group consisting of diisopropyl dimerate, glycerol monostearate, polyoxyethylene (2) cetyl ether and fatty acid amides and combinations thereof.

27. A shaving cream composition according to claim 23 wherein the preservative is selected from the group consisting of methyl paraben, propyl paraben and diazalidimyl urea and combinations thereof.

28. A shaving cream composition according to claim 23 wherein the humectant is selected from the group consisting of propylene glycol, sorbitol and glycerol and combinations thereof.

29. A shaving cream composition according to claim 23 wherein the neutralizer is selected from the group consisting of triethanolamine, propylene glycol diperlargonate and polyethylene glycol 15 cocamine and combinations thereof.

30. A shaving cream composition according to claim 23 wherein the low boiling point aliphatic hydrocarbon is selected from the group consisting of n-butane and n-pentane and combinations thereof.

31. A method of treating acne vulgaris or pseudofolliculitis barbae in humans, comprising the steps of:

applying to the skin a gel-foam shaving cream composition consisting essentially of in percent by weight:

about 0.25 to about 3% of a gelling or thickening agent;
about 7.8 to about 9.0% of a binder;
about 1% of a stabilizer;
about 2.75% of a preservative;
about 0.25 to about 50% of benzoyl peroxide;
about 13.3% of a humectant;
about 4.2 to about 4.75% of a neutralizer;
about 61.4 to 62.95% of deionized water; and
about 2.75% of a low boiling point aliphatic hydrocarbon; and removing the gel-foam shaving cream by shaving with a straight-edge razor.

* * * * *